United States Patent [19]

Abatjoglou et al.

[11] Patent Number: 4,593,011

[45] Date of Patent: * Jun. 3, 1986

[54] HYDROFORMYLATION PROCESS USING TRIARYLPHOSPHINE AND BISPHOSPHINE MONOOXIDE LIGANDS

[75] Inventors: Anthony G. Abatjoglou, Charleston; David R. Bryant, South Charleston, both of W. Va.

[73] Assignee: Union Carbide Corporation, Danbury, Conn.

[*] Notice: The portion of the term of this patent subsequent to Jun. 11, 2002 has been disclaimed.

[21] Appl. No.: 659,895

[22] Filed: Oct. 11, 1984

Related U.S. Application Data

[62] Division of Ser. No. 293,189, Aug. 17, 1981, Pat. No. 4,491,675.

[51] Int. Cl.$^4$ ............................................... B01J 31/24
[52] U.S. Cl. ....................................... 502/161; 502/166
[58] Field of Search ................................. 502/161, 166

[56] References Cited

U.S. PATENT DOCUMENTS

| | | | |
|---|---|---|---|
| 3,426,021 | 2/1969 | Seyferth | 260/246 |
| 3,527,809 | 9/1970 | Pruett et al. | 260/604 |
| 4,139,565 | 2/1979 | Unruh et al. | 260/604 HF |
| 4,148,830 | 4/1979 | Pruett et al. | 260/604 HF |
| 4,152,344 | 5/1979 | Unruh | 260/439 CY |
| 4,230,641 | 10/1980 | Bartish | 568/454 |
| 4,247,486 | 1/1981 | Brewester et al. | 568/454 |
| 4,260,828 | 4/1981 | Morrell et al. | 568/454 |
| 4,283,562 | 8/1981 | Billig et al. | 568/454 |
| 4,298,541 | 11/1981 | Oswald et al. | 260/429 R |
| 4,302,401 | 11/1981 | Oswald | 260/448 C |
| 4,400,548 | 8/1983 | Abatjoglou et al. | 502/155 X |
| 4,429,161 | 1/1984 | Abatjoglou et al. | 568/14 |
| 4,522,933 | 6/1985 | Abatjoglou et al. | 502/161 |

FOREIGN PATENT DOCUMENTS

| | | |
|---|---|---|
| 1812504 | 12/1973 | Fed. Rep. of Germany . |
| 3030108 | 4/1981 | Fed. Rep. of Germany . |
| 2014138 | 8/1979 | United Kingdom . |
| WO80/01689 | 8/1980 | PCT Int'l Appl. . |
| WO80/01690 | 8/1980 | PCT Int'l Appl. . |
| WO80/01691 | 8/1980 | PCT Int'l Appl. . |
| WO80/01692 | 8/1980 | PCT Int'l Appl. . |

OTHER PUBLICATIONS

U.S. App. Ser. No. 043,548 filed 5/29/79.
"J. of Molecular Catalysis", vol. 3, pp. 221–226, (1977/78) by A. R. Sanger.
"Platinum Metals Review", vol. 24, pp. 95 to 99, (1980) by T. B. Rauchfuss.
"Inorganic Chemistry", vol. 14, pp. 656 to 660, #3, (1975) by S. O. Grim et al.

*Primary Examiner*—Patrick P. Garvin
*Attorney, Agent, or Firm*—Reynold J. Finnegan

[57] ABSTRACT

A rhodium catalyzed hydroformylation process carried out in the presence of free triarylphosphine ligand and free organic tertiary bisphosphine monoxide ligand, and catalytic precursor solutions for said process.

7 Claims, No Drawings

HYDROFORMYLATION PROCESS USING TRIARYLPHOSPHINE AND BISPHOSPHINE MONOOXIDE LIGANDS

This application is a division of prior U.S. application Ser. No. 293,189, filing date Aug. 17, 1981, now Pat. No. 4,491,675.

FIELD OF THE INVENTION

This invention relates to an improved process for preparing aldehydes by the hydroformylation of an olefinically unsaturated organic compound in the presence of a rhodium complex catalyst free triarylphosphine ligand and free organic tertiary bisphosphine monooxide ligand.

BACKGROUND OF THE INVENTION

Processes for forming an aldehyde by the hydroformylation of an olefinically unsaturated organic compound in the presence of a rhodium-phosphorus complex catalyst and free phosphorus ligand are well known in the art, as seen, e.g., by U.S. Pat. Nos. 3,527,809; 4,148,830; and 4,247,486. The most commonly recommended phosphorus ligands are monophosphines and monophosphite compounds, especially triphenylphosphine.

In addition assignee's U.S. patent application Ser. No. 293,190, now U.S. Pat. No. 4,400,548, is directed to an improved hydroformylation process wherein organic tertiary bisphosphine monooxide ligands are employed in place of such conventional phosphorus ligands. While the use of such bisphosphine monooxide ligands furnish the process with a rhodium complex catalyst having improved high temperature stability and do improve the processing selectivity of desired linear aldehyde product in terms of amount of linear aldehyde product per given amount of olefinic starting material, such bisphosphine monooxide ligands also have the drawback of substantially reducing the reaction rate (gram moles of aldehyde product produced per liter per hour) of such hydroformylation processes in relation to that obtained when employing e.g. triphenylphosphine ligand. This disadvantage is further magnified with regard to large scale commercial type operations wherein a primary consideration in hydroformylation is the ability of the process to produce the maximum amount of aldehyde product within a given period of time rather than per given amount of olefinic starting material.

Thus practical considerations for a commercial hydroformylation process in producing normal or straight chain aldehyde product involve a balancing of such processing factors as e.g. the reaction rate, catalyst stability and the proportion of normal to branched isomeric aldehyde products formed, and the balanced optimization of such processing factors is of major importance to the state of the art.

SUMMARY OF THE INVENTION

It has now been surprisingly discovered that by employing both triarylphosphine ligand and bisphosphine monooxide ligand in the rhodium catalyzed hydroformylation of olefinically unsaturated organic starting materials excellent catalyst stability can be obtained while at the same time maintaining a high normal to branched chain isomer ratio with only a slight loss in the reaction rate of hydroformylation (catalyst activity) relative to that heretofore obtained when employing triphenylphosphine ligand alone. This ability to provide excellent catalyst stability at even high reaction temperatures without unduly adversely affecting such other primary processing factors as mentioned above affords the attainment of a much larger production of desired aldehyde over a given time period while maintaining low rhodium and low olefinically unsaturated starting material concentrations.

Thus it is an object of this invention to provide an improved rhodium complex catalyzed hydroformylation process for producing aldehydes wherein said process is conducted in the presence of both free triarylphosphine ligand and free organic tertiary bisphosphine monooxide ligand. It is also an object of this invention to provide rhodium complex catalytic precursor solutions suitable for use in said hydroformylation process. Other objects and advantages of this invention will become readily apparent from the following written description and appended claims.

Accordingly a generic aspect of this invention can be described as a process for producing aldehydes comprising hydroformylating an olefinically unsaturated compound with carbon monoxide and hydrogen in a hydroformylation reaction medium containing a rhodium complex catalyst, free triarylphosphine ligand and free organic tertiary bisphosphine monooxide ligand having the general formula

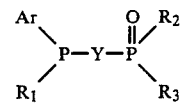

wherein Ar represents an identical or different substituted or unsubstituted aryl radical, each $R_1$, $R_2$ and $R_3$ group represents an identical or different substituted or unsubstituted monovalent hydrocarbon radical and Y represents a divalent bridging group.

Another generic aspect of this invention comprises rhodium complex catalyst precursor solutions suitable for use in said hydroformylation processes.

DESCRIPTION OF THE PREFERRED EMBODIMENTS

Basically the hydroformylation process of this invention comprises the reaction of an olefinically unsaturated compound, carbon monoxide and hydrogen in the presence of a rhodium complex catalyst, free triarylphosphine ligand and free bisphosphine monooxide ligand to produce saturated aldehydes. Such processes for forming aldehydes by the hydroformylation reaction (oxo synthesis) employing known rhodium-phosphorus complex catalysts and free phosphorus ligand are well known in the art as seen, for example, by U.S. Pat. Nos. 3,527,809, 4,148,830 and 4,247,486. Accordingly, the reaction conditions and processing techniques for this invention may correspond to any of the known reaction conditions and processing techniques heretofore employed in conventional hydroformylation reactions designed to produce aldehydes, since such conditions are not critical to this invention.

For instance, the hydroformylation process can be conducted in continuous, semi-continuous, or batch fashion and involve a liquid recycle or gas recycle operation as desired. Likewise, the manner or order of addition of the reaction ingredients, catalyst and solvent are also not critical and may be accomplished in any conventional fashion.

In general, the hydroformylation reaction is preferably carried out in a liquid reaction medium that contains a solvent for the catalyst preferably one in which both the olefinically unsaturated compound and free phosphorus ligand are substantially soluble.

The reaction conditions for effecting the hydroformylation process of this invention can be those heretofore conventionally used and may comprise a reaction temperature of from about 45° C. to about 200° C. and pressures of from about 1 to 10,000 psia. However, the preferred hydroformylation process of this invention will be that process which is most efficient in producing normal aldehyde isomer product, i.e., straight chained aldehyde as distinguished from its isomeric or branched chain aldehyde product. The optimization of the reaction conditions necessary to achieve the best results and efficiency desired will be well within the knowledge of one skilled in the art and easily obtainable by following the more preferred aspects of this invention as explained more fully below and/or by simple routine experimentation.

For instance, the total gas pressure of hydrogen, carbon monoxide and hydrogen of the hydroformylation process of this invention may range from about 1 to about 10,000 psia. More preferably however the present process of this invention is operated at low pressures, the preferred total gas pressure of hydrogen, carbon monoxide and olefinic unsaturated compound being less than about 1500 psia, more preferably less than about 500 psia and most preferably less than about 350 psia. While the minimum total pressure of the reactant gases is not particularly critical and is limited predominantly only by the amount of reaction gases necessary to obtain a desired rate of reaction, the partial pressure of the carbon monoxide employed and the overall efficiency of hydroformylation desired. For instance in the hydroformylation of allyl alcohol to its desired straight chain aldehyde it is preferred to employ a reaction temperature of about 45° C. to about 150° C. and most preferably about 60° C. to about 100° C. On the other hand reaction temperatures of about 50° C. to about 145° C. and more preferably from about 90° C. to about 120° C. have been conventionally advanced for the hydroformylation of α-olefins and α,ω-dienes. While said reaction temperatures can be employed by the process of this invention, due to the high thermal stability of the rhodium complex catalyst present in this invention it has been found that the hydroformylation of α-olefins and α,ω-dienes can be carried out at even higher temperatures such as preferably from about 120° C. to about 200° C. and more preferably from about 125° C. to about 150° C.

The triarylphosphine ligands employable in this invention and/or methods for their preparation are well known in the art and may be represented by the formula Ar$_3$P wherein each Ar radical represents an identical or different substituted or unsubstituted aryl radical. Such aryl radicals may contain from 6 to 12 carbon atoms, the most preferred aryl radical being phenyl, (C$_6$H$_5$—). Illustrative substituent groups that may be present on the aryl radicals, include e.g. alkyl radicals, alkoxy radicals, silyl radicals such as —Si(R$_4$)$_3$; amino radicals such as —N(R$_4$)$_2$; acyl radicals such as —C(O)R$_4$; carboxy radicals such as —C(O)OR$_4$; acyloxy radicals such as —OC(O)R$_4$; amido radicals such as —C(O)N(R$_4$)$_2$ and —N(R$_4$)C(O)R$_4$; sulfonyl radicals such as —SO$_2$R$_4$; ether radicals such as —OR$_4$; thionyl ether radicals such as —SR$_4$ as well as halogen, nitro, cyano, trifluoromethyl and hydroxy radicals, and the like, wherein each R$_4$ individually represents the same or different substituted or unsubstituted monovalent hydrocarbon radical having the same meaning as defined for R$_1$, R$_2$ and R$_3$ below, with the proviso that in amino substituents such as —N(R$_4$)$_2$, each R$_4$ taken together can also represent a divalent bridging group that forms a heterocyclic radical with the nitrogen atom and in amido substituents such as C(O)N(R$_4$)$_2$ and —N(R$_4$)C(O)R$_4$ each —R$_4$ bonded to N can also be hydrogen. Illustrative aryl radicals represented by Ar include e.g. phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, dimethylcarbamylphenyl, tolyl, xylyl, and the like. Illustrative triarylphosphines include, e.g. triphenylphosphine, tris-p-tolyl phosphine, tris-p-methoxyphenylphosphine, tris-p-fluorophenylphosphine, tris-p-chlorophenylphosphine, tris-dimethylaminophenylphosphine, and the like, the most preferred triarylphosphine being triphenylphosphine.

The organic tertiary bisphosphine monooxide ligands employable in this invention as noted above are those having the general formula

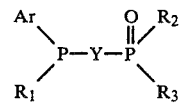

wherein Ar group represents an identical or different substituted or unsubstituted aryl radical, each R$_1$, R$_2$ and R$_3$ group represents an identical or different substituted or unsubstituted monovalent hydrocarbon radical and Y represents a divalent bridging group.

Such types of bisphosphine monooxides may be prepared by various conventional methods. For example a corresponding organic tertiary bisphosphine starting material can be oxidized with any suitable oxygenating agent such as oxygen or air, and the like to produce a mixture of monooxidized and dioxidized bisphosphines and the desired bisphosphine monooxide recovered and isolated from such mixtures by any suitable method such as crystallization, distillation, and the like. Another method for preparing bisphosphine monooxides which may be employed comprises the free radical addition of secondary phosphine oxides (e.g.

wherein R$_2$ and R$_3$ are as defined herein) with unsaturated tertiary phosphines (e.g. Ar(R$_1$-)P—Y—CH=CH$_2$ wherein AR, R$_1$ and Y are as defined herein), e.g. note PCT, International Publication Number 40 80/01690 published Aug. 21, 1980. Alternative methods of preparing certain organic tertiary bisphosphine monooxides are found disclosed e.g. in U.S. Pat. No. 3,426,021, "Unsymmetrical Bis-Phosphorus Ligands", by S. O. Grim et al, *Inorganic Chemistry*, Vol. 14, pp. 656–660 (1975) and "Abnormal Hydrolysis of Cyclic Phosphonium Salts", by A. M. Aguiar et al, *J. Amer. Chem. Soc.*, Vol. 87, pp. 671–673 (1965).

More preferably the organic tertiary bisphosphine monooxide ligands employable in this invention can be prepared by the novel procedure disclosed in assignee's U.S. patent application Ser. No. 293,145, now U.S. Pat. No. 4,429,161. Said procedure comprises reacting a corresponding organic tertiary bisphosphine (e.g. $Ar_2P-Y-P-R_2R_3$ wherein Ar, $R_2$, $R_3$ and Y are as defined herein) with an organic monofunctional alkylating agent (e.g. a monovalent hydrocarbon halide such as an alkyl or aralkyl chloride, bromide or iodide, the preferred alkylating agent being benzyl bromide) in the presence of a suitable solvent for the bisphosphine starting material (e.g., a hydrocarbon solvent such as toluene) to form an insoluble monophosphonium salt of the bisphosphine starting material which can be easily recovered by any suitable method such as filtration. The intermediate monophosphonmium salt is then hydrolyzed with an aqueous alkaline solution (e.g., 1 to 20 percent by weight of an alkali metal or alkaline earth metal hydroxide such as sodium hydroxide in water) to the desired organic tertiary bisphosphine monooxides employable in this invention. The bisphosphine monooxide product is a water insoluble precipitate that can be recovered by any suitable method such as filtration. Both procedural steps of said process are preferably conducted under nitrogen atmosphere and are essentially stoichiometric quantitative type reactions. However, while it is preferred to employ only about one mole of alkylating agent per mole of the bisphosphine starting material employed, it is preferred to employ an excess amount of water (e.g., from about a 100 percent stoichiometric excess on up to about a 10,000 percent stoichiometric excess or higher may be employed) in the hydrolysis step above that theoretical stoichiometrical amount of water necesary to hydrolyze the monophosphonium salt to its desired bisphosphine monooxide product. The formation of the intermediate monophosphonium salt can be carried out at any suitable temperature such as from about 20° C. up to the boiling point of the solvent, while the hydrolysis procedure can also be carried out at any suitable temperature such as from about 20° C. to 100° C. This procedure is very efficient for preparing large yields of selectivity desired bisphosphine monooxides and can be found more fully described in said Ser. No. 293,145, now Pat. No. 4,429,161, the entire disclosure of which is incorporated herein by reference thereto. Of course the organic tertiary bisphosphine starting materials and/or methods for their preparation are well known in the art.

Illustrative aryl radicals represented by the Ar group in the above bisphosphine monooxide formulas include both substituted and unsubstituted aryl groups. Such aryl radicals may contain from 6 to 12 carbon atoms, the most preferred aryl radical being phenyl, ($C_6H_5-$). Illustrative substituent groups that may be present on the aryl radicals, include e.g. alkyl radicals, alkoxy radicals, silyl radicals such as $-Si(R_4)_3$; amino radicals such as $-N(R_4)_2$; acyl radicals such as $-C(O)R_4$; carboxyl radicals such as $-C(O)OR_4$; acyloxy radicals such as $-OC(O)R_4$; amido radicals such as $-C(O)N(R_4)_2$ and $-N(R_4)C(O)R_4$; sulfonyl radicals such as $-SO_2R_4$; ether radicals such as $-OR_4$, thionyl ether radicals such as $-SR_4$ as well as halogen, nitro, cyano, trifluoromethyl and hydroxy radicals, and the like, wherein each $R_4$ individually represents the same or different substituted or unsubstituted monovalent hydrocarbon radical having the same meaning as defined for $R_1$, $R_2$ and $R_3$ below, with the proviso that in amino substituents such as $-N(R_4)_2$, each $R_4$ taken together can also represent a divalent bridging group that forms a heterocyclic radical with the nitrogen atom and in amido substituents such as $C(O)N(R_4)_2$ and $-N(R_4)C(O)R_4$ each $-R_4$ bonded to N can also be hydrogen. Illustrative aryl radicals represented by Ar include e.g. phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, dimethylcarbamylphenyl, tolyl, xylyl, and the like. Most preferably the Ar radical is phenyl.

Monovalent hydrocarbon radicals represented by $R_1$, $R_2$ and $R_3$, in the above formulas include those containing from 1 to 30 carbon atoms such as substituted or unsubstituted alkyl, aryl, alkaryl, aralkyl and alicyclic radicals. Among the more specific unsubstituted monovalent hydrocarbon radicals that may be mentioned are alkyl radicals including primary, secondary and tertiary alkyl radicals such as methyl, ethyl, n-propyl, isopropyl, butyl, sec-butyl, t-butyl, t-butylethyl, t-butylpropyl, n-hexyl, amyl-, sec-amyl, t-amyl, iso-octyl, decyl, dodecyl, octadecyl, eicosyl, and the like; aryl radicals such as phenyl, naphthyl and the like, aralkyl radicals such as benzyl, phenylethyl, triphenylmethylethane and the like, alkaryl radicals such as tolyl, xylyl, and the like; and alicyclic radicals such as cyclopentyl, cyclohexyl, cyclooctyl, cyclohexylethyl, and the like. In addition such monovalent hydrocarbon radicals may be substituted with any substituent which does not unduly adversely effect the process of this invention. Suitable illustrative substituents that may be on the hydrocarbon radical are for example silyl radicals such as $-Si(R_4)_3$; amino radicals such as $-N(R_4)_2$; acyl radicals such as $-C(O)R_4$; acyloxy radicals such as $-OC(O)R_4$; amido radicals such as $-C(O)N(R_4)_2$ and $-N(R_4)C(O)R_4$; sulfonyl radicals such as $-SO_2R_4$; ether radicals such as $-OR_4$, thionyl ether radicals such as $-SR_4$ as well as halogen, nitro, cyano, trifluoromethyl and hydroxy radicals, and the like, wherein each $P_4$ individually represents the same or different substituted or unsubstituted monovalent hydrocarbon radical having the same meaning as defined for $R_1$, $R_2$ and $R_3$, with the proviso that in amino substituents such as $-N(R_4)_2$, each $R_4$ taken together can also represent a divalent bridging group that forms a heterocyclic radical with the nitrogen atom and in amido substituents such as $C(O)N(R_4)_2$ and $-N(R_4)C(O)R_4$ each $R_4$ bonded to N can also be hydrogen. Illustrative substituted monovalent hydrocarbon radicals include e.g., $-(CH_2)_2Si(CH_3)_3$,      $-(CH_2)_3Si(CH_3)_3$,
$-(CH_2)_2Si(C_3H_7)_3$,    $-(CH_2)_2Si(C_6H_5)_3$,
$-(CH_2)_2C(O)CH_3$,        $-(CH_2)C(O)C_2H_5$,
$-(CH_2)_2C(O)C_6H_5$,      $-(CH_2)_2OC(O)C_6H_5$,
$-(CH_2)_2OC(O)CH_3$,       $-(CH_2)_2N(C_2H_5)_2$,

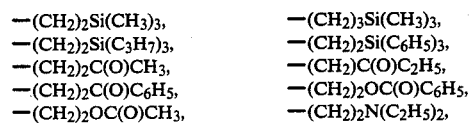
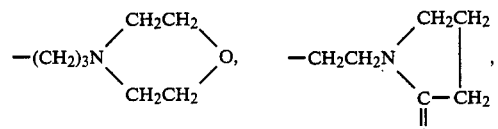

-continued

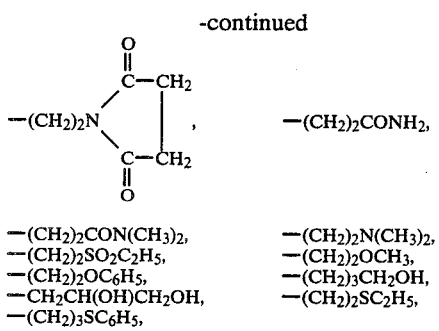  —(CH₂)₂CONH₂,

—(CH₂)₂CON(CH₃)₂,  —(CH₂)₂N(CH₃)₂,
—(CH₂)₂SO₂C₂H₅,  —(CH₂)₂OCH₃,
—(CH₂)₂OC₆H₅,  —(CH₂)₃CH₂OH,
—CH₂CH(OH)CH₂OH,  —(CH₂)₂SC₂H₅,
—(CH₂)₃SC₆H₅, as well as fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl, furyl, pyryl, methoxyethylphenyl, acetamidophenyl, dimethylcarbamylphenyl, and the like.

The more preferred substituted and unsubstituted monovalent hydrocarbon radicals represented by $R_1$, $R_2$, $R_3$ and $R_4$ are alkyl radicals having from 1 to 12 carbon atoms and aryl radicals having from 6 to 12 carbon atoms, the most preferred radicals being unsubstituted monovalent hydrocarbon radicals and the most preferred aryl radical being phenyl.

In general the more preferred organic tertiary bisphosphine monooxides are those such as wherein $R_1$, $R_2$ and $R_3$ all represent an aryl radical, especially phenyl ($C_6H_5$—).

The divalent bridging group represented by Y in the above formulas is a divalent radical containing from 1 to 30 carbon atoms selected from the group consisting of hydrocarbon radicals, oxygen containing hydrocarbon radicals (i.e. hydrocarbon radicals interrupted with an oxygen atom), sulfur containing hydrocarbon radicals (i.e. hydrocarbon radicals interrupted with a sulfur atom) and nitrogen containing hydrocarbon atoms (i.e. hydrocarbon radicals interrupted with a nitrogen atom). Preferably such radicals contain from 1 to 12 carbon atoms. Illustrative divalent hydrocarbon radicals include alkylene radicals (e.g. methylene (—CH₂—), ethylene, propylene, isopropylene, butylene, 1,2-dimethylethylene, t-butylene, neopentylene, 2-methylpropylene, hexylene, 2-ethylhexylene, dodecylene, eicosylene, and the like); arylene radicals (e.g. phenylene, diphenylene, and the like); as well as alkylene containing arylene radicals (e.g. methylenephenylene (—CH₂C₆H₄—), ethylenephenylethylene (—C₂H₄C₆H₄—C₂H₄—), phenylenepropylphenylene (—C₆H₄C(CH₃)₂C₆H₄—), and the like); alkylidene radicals (e.g. ethylidene (—CH=CH—), and the like); and the like. Illustrative oxygen containing hydrocarbon radicals include alkyleneoxyalkylene radicals (e.g. ethylene-oxymethylene (—C₂H₄OCH₂—), propyleneoxymethylene (—C₃H₆OCH₂—), ethyleneoxyethylene (—C₂H₄OC₂H₄—), 1,2-bis(ethyleneoxy)ethane (—C₂H₄OC₂H₄OC₂H₄—), propyleneoxypropylene (—C₃H₆OC₃H₆—) and the like); aryleneoxyalkylene radicals (e.g. phenyleneoxymethylene (—C₆H₄OCH₂—), and the like); and the like. Illustrative sulfur or thio containing hydrocarbon radicals include alkylenethioalkylene radicals (e.g. ethylenethioethylene (—C₂H₄SC₂H₄—), 1,2-bis(ethylenethio)ethane (—C₂H₄SC₂H₄SC₂H₄—), propylenethiomethylene (—C₃H₆SCH₂—), propylenethiopropylene (—C₃H₆SC₃H₆—), and the like); arylenethioalkylene radicals (e.g. phenylenethiomethylene (—C₃H₆SCH₂—), and the like); and the like. Illustrative amino containing hydrocarbon radicals include alkyleneaminoalkylene radicals (e.g., methyleneaminomethylethylene (—CH₂N(CH₃)C₂H₄—), ethyleneaminomethylethylene (—C₂H₄N(CH₃)C₂H₄—), bis(ethyleneaminomethyl)ethane (—C₂H₄N(CH₃)C₂H₄N(CH₃)C₂H₄—), propyleneamino methylpropylene (—C₃H₆N(CH₃)C₃H₆—) and the like. Preferably Y is a divalent hydrocarbon radical, especially a divalent alkylene radical containing from 2 to 8 carbon atoms.

Illustrative examples of such organic ditertiary bisphosphine monooxides include, e.g.

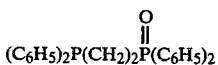

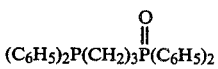

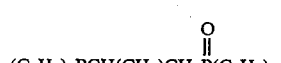

-continued

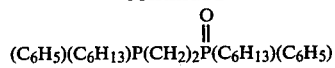
$(C_6H_5)(C_6H_{13})P(CH_2)_2\overset{O}{\overset{\|}{P}}(C_6H_{13})(C_6H_5)$

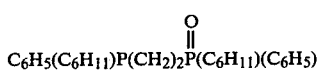
$C_6H_5(C_6H_{11})P(CH_2)_2\overset{O}{\overset{\|}{P}}(C_6H_{11})(C_6H_5)$

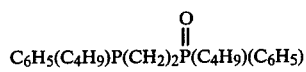
$C_6H_5(C_4H_9)P(CH_2)_2\overset{O}{\overset{\|}{P}}(C_4H_9)(C_6H_5)$

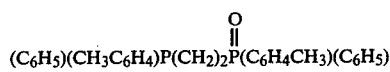
$(C_6H_5)(CH_3C_6H_4)P(CH_2)_2\overset{O}{\overset{\|}{P}}(C_6H_4CH_3)(C_6H_5)$

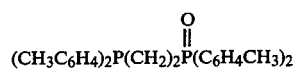
$(CH_3C_6H_4)_2P(CH_2)_2\overset{O}{\overset{\|}{P}}(C_6H_4CH_3)_2$

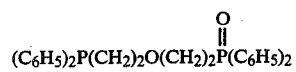
$(C_6H_5)_2P(CH_2)_2O(CH_2)_2\overset{O}{\overset{\|}{P}}(C_6H_5)_2$

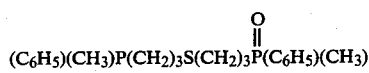
$(C_6H_5)(CH_3)P(CH_2)_3S(CH_2)_3\overset{O}{\overset{\|}{P}}(C_6H_5)(CH_3)$

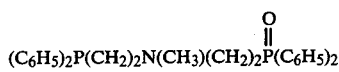
$(C_6H_5)_2P(CH_2)_2N(CH_3)(CH_2)_2\overset{O}{\overset{\|}{P}}(C_6H_5)_2$

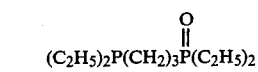
$(C_2H_5)_2P(CH_2)_3\overset{O}{\overset{\|}{P}}(C_2H_5)_2$

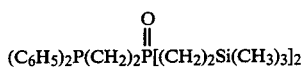
$(C_6H_5)_2P(CH_2)_2\overset{O}{\overset{\|}{P}}[(CH_2)_2Si(CH_3)_3]_2$

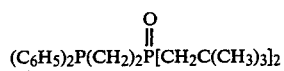
$(C_6H_5)_2P(CH_2)_2\overset{O}{\overset{\|}{P}}[CH_2C(CH_3)_3]_2$

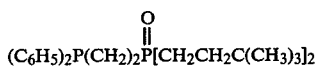
$(C_6H_5)_2P(CH_2)_2\overset{O}{\overset{\|}{P}}[CH_2CH_2C(CH_3)_3]_2$

$(C_6H_5)_2PCH_2\overset{O}{\overset{\|}{P}}(CH_3)_2$

$(C_6H_5)_2PCH_2\overset{O}{\overset{\|}{P}}(C_2H_5)_2$

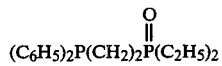
$(C_6H_5)_2P(CH_2)_2\overset{O}{\overset{\|}{P}}(C_2H_5)_2$

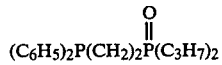
$(C_6H_5)_2P(CH_2)_2\overset{O}{\overset{\|}{P}}(C_3H_7)_2$

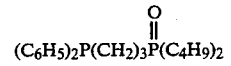
$(C_6H_5)_2P(CH_2)_3\overset{O}{\overset{\|}{P}}(C_4H_9)_2$

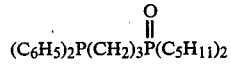
$(C_6H_5)_2P(CH_2)_3\overset{O}{\overset{\|}{P}}(C_5H_{11})_2$

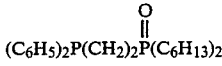
$(C_6H_5)_2P(CH_2)_2\overset{O}{\overset{\|}{P}}(C_6H_{13})_2$

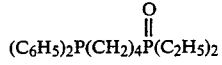
$(C_6H_5)_2P(CH_2)_4\overset{O}{\overset{\|}{P}}(C_2H_5)_2$ $(C_6H_5)P(CH_2)_5\overset{O}{\overset{\|}{P}}(C_2H_5)_2$ -continued

$(C_6H_5)_2P(CH_2)_2\overset{O}{\overset{\|}{P}}[(CH_2)_2C(O)CH_3]_2$

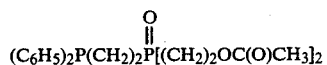
$(C_6H_5)_2P(CH_2)_2\overset{O}{\overset{\|}{P}}[(CH_2)_2OC(O)CH_3]_2$

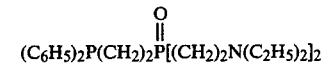
$(C_6H_5)_2P(CH_2)_2\overset{O}{\overset{\|}{P}}[(CH_2)_2N(C_2H_5)_2]_2$

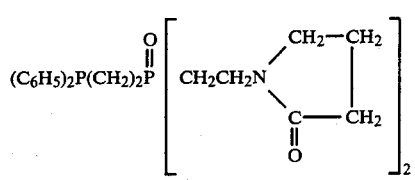

$(C_6H_5)_2P(CH_2)_2\overset{O}{\overset{\|}{P}}[(CH_2)_2CONH_2]_2$

$(C_6H_5)_2P(CH_2)_2\overset{O}{\overset{\|}{P}}[(CH_2)_2SO_2C_2H_5]_2$

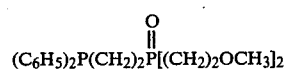
$(C_6H_5)_2P(CH_2)_2\overset{O}{\overset{\|}{P}}[(CH_2)_2OCH_3]_2$

$(C_6H_5)_2P(CH_2)_2\overset{O}{\overset{\|}{P}}[(CH_2)_3CH_2OH]_2$

$(C_6H_5)_2P(CH_2)_2\overset{O}{\overset{\|}{P}}[(CH_2)_2SC_2H_5]_2$

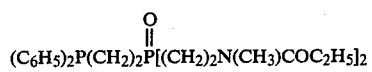
$(C_6H_5)_2P(CH_2)_2\overset{O}{\overset{\|}{P}}[(CH_2)_2N(CH_3)COC_2H_5]_2$

$(C_6H_5)_2P(CH_2)_2(C_6H_5)(CH_2)_2\overset{O}{\overset{\|}{P}}(C_6H_5)_2$

$(C_6H_5)_2P(CH_2)_4\overset{O}{\overset{\|}{P}}(C_2H_5)_2$

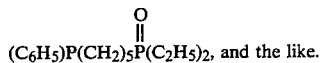
$(C_6H_5)P(CH_2)_5\overset{O}{\overset{\|}{P}}(C_2H_5)_2$, and the like.

The rhodium complex catalyst present in the hydroformylation process of this invention consists essentially of a rhodium-phosphorus ligand complex, said phosphorus ligand being derived from the same triarylphosphine and/or the-same organic tertiary bisphosphine monooxide ligands already herein defined above. While it is not certain as to the exact nature of the active rhodium-phosphorus ligand complex catalyst and while it is not intended to limit the present invention to any single explanation, theory or mechanistic discourse of how the rhodium is complexed with the triarylphosphine and/or bisphosphine monooxide, it appears that the active catalyst in its simplest form consists essentially of a concentration of triarylphosphine ligand and/or organic tertiary bisphosphine monooxide ligand and carbon monoxide equal to a total of four moles in complex combination with one mole of rhodium. Of course it is to be understood that the term "complex" means a coordination compound formed by the union of one or more electronically rich molecules or atoms capable of independent existence with one or more electronically poor molecules or atoms, each of which is also capable of independent existence. Thus the active species may comprise a complex catalyst mixture, in their monomeric forms, which are characterized by one, two and/or three phosphorus ligand molecules complexed with one molecule of rhodium. As can be surmised from the above discussion, carbon monoxide (which is also properly classified as a ligand) is likewise present and complexed with the rhodium in the active species. Furthermore, the active catalyst species may also contain hydrogen as a ligand. Thus the ultimate composition of the active complex species can be likened or attributed to the outcome of competing reactions between carbon monoxide and both phosphorus ligands for "complexing sites" with the rhodium element and these competing reactions can be disturbed or influenced, within significant limits, by increasing or decreasing the partial pressure due to carbon monoxide, or by increasing or decreasing the concentration of the triarylphosphine and/or bisphosphine monooxide ligand. As a generalized statement therefore, the component (carbon monoxide or phosphorus ligand) which can shift the equilibrium of the competing reaction in its favor should enjoy the greater opportunities of occupying the "complexing sites" with rhodium to give the active complex catalyst. Moreover one could view the function of the free triarylphosphine ligand and/or organic tertiary bisphosphine monooxide ligand as either maintaining the status quo of the various forms of active complex catalyst during the hydroformylation, or as a means for shifting the equilibrium of the competing reactions in its favor and therefore causing additional phosphorus ligand to enter into the complex combination with rhodium with the probable eviction of a similar number of carbon monoxide ligands from the complex catalyst. In addition it is believed that unlike triphenylphosphine, the organic tertiary bisphosphine monooxide ligands of this invention are weakly chelated to the rhodium through their phosphorus-monooxide groups

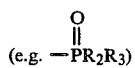

(e.g. $-\overset{\overset{O}{\|}}{P}R_2R_3$)

in addition to being strongly coordinated to the rhodium through their non-oxygenated phosphorus groups (e.g. $ArR_1P-$). Thus it is believed that while the active rhodium complex catalyst may comprise a mixture of different rhodium species, e.g. species wherein the phosphorus ligand is exclusively triarylphosphine and/or species wherein the phosphorus ligand is exclusively bisphosphine monooxide, it is believed that the predominate rhodium complex species is one which contains at least one triarylphosphine ligand and at least one organic tertiary bisphosphine monooxide ligand bonded to the same rhodium atom. Moreover, as in the case with prior art rhodium-phosphorus complex catalysts the rhodium complex catalysts of this invention can be formed by methods known in the art. For example, preformed stable rhodium hydridocarbonyltris(triarylphosphine-bisphosphine monooxide) catalysts may be introduced into the reaction medium of the hydroformylation process. Such preformed catalysts may be prepared by reacting conventional triarylphosphine rhodium carbonyl hydrides e.g. hydridocarbonyltris-triphenylphosphine rhodium, with an organic tertiary bisphosphine monooxide ligand as defined herein in the presence of a suitable hydrocarbon solvent to effect a phosphorus ligand interchange. Alternatively, and this is preferred, the rhodium complex catalysts of this invention can be derived from a rhodium catalyst precursor such as rhodium dicarbonyl acetylacetonate, $Rh_2O_3$, $Rh_4(CO)_2$, $Rh_6(CO)_{16}$, $Rh(NO_3)_3$ and the like which may be introduced into the reaction medium along with the triarylphosphine and bisphosphine monooxide ligands for the in situ formation of active catalyst. In a preferred embodiment rhodium dicarbonyl acetylacetonate is employed as a rhodium precursor and reacted in the presence of a solvent with a mixture of triarylphosphine and organic tertiary bisphosphine monooxide to form a catalytic rhodium carbonyl phosphorus ligand acetylacetonate precursor which is introduced into the reactor along with excess free triarylphosphine and organic tertiary bisphosphine monooxide ligand for the in situ formation of the active catalyst. Of course it is to be further understood that the active catalyst of the process of this invention may also be formed in situ during hydroformylation by incorporating bisphosphine monooxide ligand into a hydroformylation process that has been employing a rhodium-triarylphosphine ligand complex catalyst as well as by incorporating triarylphosphine ligand into a hydroformylation process that has been employing a rhodium-bisphosphine monooxide ligand complex catalyst. Thus in any event it is sufficient for the purpose of this invention to understand that carbon monoxide, hydrogen, triarylphosphine and organic tertiary bisphosphine monooxide are all ligands that are capable of being complexed with the rhodium and that an active rhodium-phosphorus ligand complex catalyst is present in the reaction medium under the conditions of hydroformylation.

Accordingly more specifically the rhodium complex catalysts of this invention may be defined as consisting essentially of rhodium complexed with carbon monoxide, a triarylphosphine and/or an organic tertiary bisphosphine monooxide ligand as defined herein. Of course it is to be understood that the catalyst terminology "consisting essentially of" is not meant to exclude, but rather include, hydrogen complexed with the rhodium, in addition to carbon monoxide and the phosphorus ligands. However, such terminology is meant to exclude other materials in amounts which unduly adversely poison or unduly deactivate the catalyst and thus most desirably is free of contaminants such as rhodium-bound halogen e.g. chlorine, and the like. The hydrogen and/or carbonyl ligands of an active rhodium complex catalyst may be present as a result of being ligands bonded to a precursor catalyst and/or as a result of in situ formation due to the hydrogen and carbon monoxide gases employed in the hydroformylation process. Likewise as in the case of containing hydroformylation process that has employed a rhodium triarylphosphine catalyst which results in the in situ formation of alkyl substituted arylphosphine ligands as explained in U.S. Pat. No. 4,260,828 during the hydroformylation process, it may be possible that some alkyl substituted arylphosphine ligands and/or alkyl substituted aryl bisphosphine monooxides (i.e. ligands wherein one the aryl groups of e.g., a $Ar_2P$-group of an originally employed bisphosphine monooxide ligand has been replaced by an alkyl radical e.g. corresponding to the olefinically unsaturated starting material to be hydroformylated) are produced in situ in the hydroformylation process of this invention. Thus it should be understood that the active rhodium catalyst of this invention and the catalyst terminology "consisting essentially of" is also not meant to exclude, but include the possible presence of such types of alkyl substituted arylphosphine ligands and/or alkyl substituted aryl bisphosphine monoxide ligands complexed to the rhodium as well as other above mentioned complexing ligands.

Moreover it is clear that the amount of rhodium-phosphorus ligand complex catalyst present in the hydroformylation medium of the process of this invention need only be that minimum amount which is necessary to provide the rhodium concentration (which concentration in general may range from about 25 ppm to about 1000 ppm, and more preferably from about 50 to about 400 ppm of rhodium calculated as free metal) desired to be employed and which will furnish the basis for at least that catalytic amount of rhodium necessary to catalyze the particular hydroformylation process desired.

The olefinically unsaturated organic compounds that may be hydroformylated by the process of this invention as well as methods for their preparation are well known in the art and may contain from 2 to 20 carbon atoms. Said olefinic compounds are characterized by an internal or terminal ethylenic carbon to carbon bond, including alpha-olefins in which the terminal ethylenic group is a vinylidene group

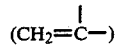

or a vinyl group ($CH_2=CH—$). Said olefins may be straight chain or branched chain and may contain groups or substituents which do not essentially interfere whith the course of the hydroformylation process, such as

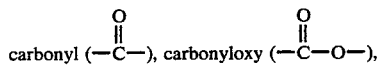

oxy (—O—), hydroxy(—OH), carboxy (—COOH), halo, alkoxy, phenyl, haloalkyl, and the like. Moreover said olefins may contain one or more ethylenic bonds.

Illustrative alpha olefinic compounds which can be employed as reactants include ethylene, propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, 1,5-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, vinyl ethyl ether, vinyl methyl ether, allyl ethyl ether, n-propyl 7-octenoate, 3-butenoic acid, 7-octenoic acid, 3-butenenitrile, 5-hexenamide and the like. Illustrative internal olefinic compounds which can be employed as reactants include 2-pentene, 2-hexene, 3-hexene, 3-octene, 2-methyl-2-pentene, 3-hexen-1-ol, cyclohexene, and stilbene, and the like. Preferred alpha olefinic compounds include alkenes, alkyl alkenoates, alkenyl alkanoates, alkenyl alkyl ethers and alkenols. The most preferred olefinic starting materials are alpha alkenes.

As noted above the hydroformylation process of this invention is carried out in the presence of both free triarylphosphine ligand and free organic tertiary bisphosphine monoxide ligand. The term "free ligand" as employed herein means ligand that is not tied or complexed with the rhodium of the rhodium complex catalyst of this invention. Of course said free triarylphosphine ligand and said free bisphosphine monooxide ligand may correspond to any of the above triarylphosphines and bisphosphine monooxides discussed above. Thus the triarylphosphine ligands and organic tertiary bisphosphine ligands defined herein are employed in this invention as both the phosphorus ligand of the rhodium-phosphorus complex catalyst of the hydroformylation process of this invention as well as the free phosphorus ligand present in the reaction medium of the hydroformylation process of this invention. In addition is it to be understood that while the phosphorus ligand of the rhodium-phosphorus complex catalyst and the free phosphorus ligand present in a given process of this invention are normally of the same type of triarylphosphine and/or bisphosphine monooxide, different types of triarylphosphines and/or bisphosphine monooxides as well as, mixtures of two or more different triarylphosphines and/or bisphosphine monooxides may be employed for each purpose in any given process if desired. The mole ratio of total free phosphorus ligand (i.e. free triarylphosphine ligand plus free bisphosphine monooxide ligand) per mole of catalytically active rhodium present in the hydroformylation reaction medium of this invention may be as little as about 10:1, while the upper limit does not appear to be critical and its concentration would be dictated largely by commercial, economic and solubility considerations. More preferably mole ratios of total phosphorus ligand per mole of catalytically active rhodium present in the hydroformylation reaction medium ranging from about 50:1 to 2000:1 should be sufficient for most purposes. On the other hand the mole ratio of free triarylphosphine ligand to free organic tertiary bisphosphine monooxide ligand present in the hydroformylation reaction medium of the hydroformylation process of this invention may range from about 2:1 to about 30:1 more preferably from about 5:1 to about 15:1.

The hydroformylation process of this invention is also preferably conducted in the presence of an organic solvent for the rhodium-phosphorus catalyst. Any suitable solvent which does not unduly adversely interfere with the intended hydroformylation process can be employed. Such solvents may include those heretofore commonly employed in known hydroformylation processes such as e.g. disclosed in U.S. Pat. Nos. 3,527,809 and 4,148,830. Of course mixtures of one or more different catalytic solvents may be employed if desired. In general it is preferred to employ aldehyde compounds corresponding to the aldehyde products desired to be produced (e.g. n-butyraldehyde) and/or higher boiling aldehyde condensation by-products as the primary solvent such as the higher boiling aldehyde liquid condensation by-products that are produced in situ during the hydroformylation process (e.g. butyraldehyde trimers). Such aldehyde condensation products can also be preformed if desired and used accordingly. Moreover such higher boiling aldehyde condensation by-products and methods for their preparation are more fully described in U.S. Pat. Nos. 4,148,830 and 4,247,486. Of course it is obvious that the amount of solvent employed is not critical to the subject invention and need only be that amount sufficient to provide the hydroformylation reaction medium with the particular rhodium concentration desired for said hydroformylation process. In general the amount of solvent when employed may range from about 5 percent by weight up to about 95 percent by weight or more based on the total weight of the hydroformylation reaction medium.

It is generally preferred to carry out the hydroformylation process of this invention in a continuous manner. Such continuous hydroformylation processes are well known in the art and may involve a liquid recycle or gas recycle operation as desired.

A further aspect of this invention can be described as a catalyst precursor composition consisting essentially of a solubilized rhodium carbonyl phosphorus acetylacetonate complex precursor catalyst, an organic solvent, free triarylphosphine, and free organic tertiary bisphosphine monooxide. Such precursor compositions are prepared by forming a solution of rhodium dicarbonyl acetylacetonate, an organic solvent, a triarylphosphine and an organic tertiary bisphosphine monooxide as defined herein. The triarylphosphine or bisphosphine monooxide readily replaces one of the dicarbonyl ligands of the rhodium-acetylacetonate complex precursor at room temperature as witnessed by the evolution of carbon monoxide gas. This substitution reaction may be facilitated by heating the solution if desired. Any suitable solvent in which both the rhodium-dicarbonyl acetylacetonate complex precursor and rhodium carbonyl phosphorus acetylacetonate complex precursor are soluble can be employed. Suitable solvents of course include and are preferably those employable in the hydroformylation process of this invention. Accordingly the amounts of rhodium complex catalyst precursor, organic solvent, triarylphosphine and bisphosphine monooxide, as well as their preferred embodiments present in such catalyst precursor compositions may obviously correspond to those amounts employable in the hydroformylation process of this invention and which have already been discussed herein above. Experience has shown that the acetylacetonate ligand of the precursor catalyst is very quickly replaced, within a matter of minutes, after the hydroformylation process has begun with a different ligand e.g. hydrogen, carbon monoxide, or phosphorus ligand, to form the active rhodium complex catalyst as explained above. The acetylacetone which is quickly freed from the precursor catalyst under hydroformylation conditions is removed from the reaction medium with the product aldehyde and thus is in no way detrimental to the hydroformylation process. The use of such preferred rhodium complex catalytic precursor compositions thus provide a simple economical and efficient method for handling the rhodium precursor metal and hydroformylation start-up.

Finally, the aldehyde products of the hydroformylation process of this invention have a wide range of utility that is well known and documented in the prior art e.g. they are especially useful as starting materials for the production of alcohols.

The following examples are illustrative of the present invention and are not to be regarded as limitative. It is to be understood that all of the parts, percentages and proportions referred to herein and in the appended claims are by weight unless otherwise indicated.

EXAMPLES 1 TO 13

A series of long term catalyst stability experiments were conducted in a glass reactor operating in a continuous propylene hydroformylation mode. The reactor consisted of a three ounce pressure bottle submersed in an oil bath with a glass front for viewing. In each experiment about 20 ml. of a freshly prepared rhodium catalytic precursor solution was charged to the reactor with a syringe after purging the system with nitrogen. Each precursor solution contained from 100 to 200 ppm rhodium calculated as free metal (as noted in Table I below) introduced as rhodium dicarbonyl acetylacetonate, a phosphorus ligand or mixture of phosphorus ligands and a solvent. The mole ratio of total free phosphorus ligand per mole of rhodium present in each precursor solution (P/Rh) and the mole ratio of each phosphorus ligand to each other in a given phosphorus mixture are shown in TABLE I below.

The solvent employed in Examples 1 to 12 was Texanol ® (a mixture of butyraldehyde trimers), while Example 13 employed a mixture of Texanol ® and 1,4-butanediol (2:1 volume ratio). After closing the reactor, the system was again purged with nitrogen and the oil bath was heated to furnish the desired hydroformylation reaction temperature. The hydroformylation reaction in each experiment was conducted at a total gas pressure of about 165 psig, the target partial pressures of hydrogen, carbon monoxide and propylene being about 100 psia; 15 psia, and 30 psia, respectively, the remainder being nitrogen. The flows of the feed gases (carbon monoxide, hydrogen and propylene) were controlled individually with mass flow meters and the feed gases dispersed into the precursor solution via fritted glass spargers. The unreacted portion of the feed gases stripped out the product aldehydes. Examples 1 to 8 were conducted at about 105° C. for one day and then the temperature raised to about 130° C. and the hydroformylation continued for four days. Examples 9 to 13 were conducted at about 105° C. over a weekend and then the temperature was raised to about 130° C. and the hydroformylation was continued for four days. The product aldehydes for each experiment were analyzed over the first day of continuous operation at 130° C. and over the fourth day of continuous operation at 130° C. and the average reaction rates for each experiment in terms of gram moles per liter per hour of total product aldehydes for the first and fourth days of continuous operation at the average measured partial pressures of hydrogen, carbon monoxide and propylene for said days are given in TABLE I below.

The corrected reaction rates given in parenthesis a in TABLE I below were computed using the formula $$\text{Observed Reaction Rate for Day 4 at 130° C.} \times \frac{A}{B}$$

wherein A equals the value of the given observed reaction rate for day 4 at 130° C. of the experiment divided by the predicted reaction rate for day 4 at 130° C. of continuous propylene hydroformylation at the same partial pressures and reaction conditions given for the observed reaction rate for day 4 at 130° C. of the experiment, using a mathematical rate model developed for a standard rhodium-triphenylphosphine complex catalyst; and B equals the value of the given observed reaction rate for day 1 at 130° C. of the experiment divided by the predicted reaction rate for day 1 at 130° C. of continuous propylene hydroformylation at the same partial pressures and reaction conditions given for the observed reaction rate for day 1 at 130° C. of the experiment, using a mathematical rate model developed for a standard rhodium-triphenylphosphine complex catalyst.

TABLE I

| Example/Ligand | Day 130° C. | Aldehyde Product Reaction Rate gmoles/L hr | [b]% Activity Decline | $P_{CO}$ (psia) | $P_{H_2}$ (psia) | $P_{C_3H_6}$ (psia) | [Rh] ppm | P/Rh Mole Ratio |
|---|---|---|---|---|---|---|---|---|
| 1  $(C_6H_5)_3P$ | 1 | 1.74 | 42 | 15.5 | 98.5 | 27.0 | 200 | 140 |
|  | 4 | 1.12 (1.00)[a] |  | 16.5 | 99.5 | 30.0 | 200 | 140 |
| 2  $(C_6H_5)_3P/$ | 1 | 1.24 | 6.5 | 11.2 | 100.0 | 24.0 | 200 | 140 |
| $(C_6H_5)_2P(CH_2)_2P(O)(C_6H_5)_2$ | 4 | 1.08 (1.16)[a] |  | 18.5 | 101.5 | 26.5 | 200 | 140 |
| (9:1 mole ratio) |  |  |  |  |  |  |  |  |
| 3  $(CH_3C_6H_4)_3P$ | 1 | 1.36 | 25 | 15.0 | 103.0 | 26.5 | 100 | 140 |
|  | 4 | 1.49 (1.02)[a] |  | 15.0 | 93.0 | 38.5 | 100 | 140 |
| 4  $(CH_3C_6H_4)_3P/$ | 1 | 1.11 | 17 | 12.4 | 99.0 | 25.0 | 100 | 140 |
| $(C_6H_5)_2P(CH_2)_2P(O)(C_6H_5)_2$ | 4 | 1.15 (.92)[a] |  | 17.0 | 99.0 | 29.5 | 100 | 140 |
| (10:1 mole ratio) |  |  |  |  |  |  |  |  |
| 5  $(CH_3OC_6H_4)_3P$ | 1 | 1.57 | 13 | 14.0 | 100.0 | 27.0 | 200 | 140 |
|  | 4 | 1.68 (1.36)[a] |  | 18.0 | 100.5 | 30.0 | 200 | 140 |
| 6  $(CH_3OC_6H_4)_3P/$ | 1 | 1.62 | 6 | 12.0 | 102.0 | 29.3 | 200 | 140 |
| $(C_6H_5)_2P(CH_2)_2P(O)(C_6H_5)_2$ | 4 | 1.80 (1.53)[a] |  | 17.5 | 100.0 | 30.5 | 200 | 140 |
| (10:1 mole ratio) |  |  |  |  |  |  |  |  |
| 7  $(ClC_6H_4)_3P/$ | 1 | 0.53 | 54 | 14.5 | 99.5 | 29.5 | 200 | 140 |
| $(C_6H_5)_2P(CH_2)_2P(O)(C_6H_5)_2$ | 4 | 0.38 (0.24)[a] |  | 15.5 | 99.5 | 30.5 | 200 | 140 |
| (10:1 mole ratio) |  |  |  |  |  |  |  |  |
| 8  $(ClC_6H_4)_3P$ | 1 | 0.59 | 46 | 14.5 | 98.0 | 30.5 | 200 | 140 |
|  | 4 | 0.49 (.32)[a] |  | 15.0 | 94.5 | 37.0 | 200 | 140 |
| 9  $(C_6H_5)_2P(CH_2)_2P(O)(C_6H_5)_2$ | 1 | 1.06 | 40 | 12.5 | 99.5 | 26.0 | 200 | 40 |
|  | 4 | 0.87 (0.63)[a] |  | 15.5 | 99.5 | 28.5 | 200 | 40 |
| 10  $(C_6H_5)_3P/$ | 1 | 1.88 | 55 | 14.6 | 99.5 | 26.0 | 200 | 147 |
| $(C_6H_5)_2P(CH_2)_2P(O)(C_6H_5)_2$ | 4 | 1.10 (0.85)[a] |  | 18.0 | 100.0 | 29.0 | 200 | 147 |
| (29:1 mole ratio) |  |  |  |  |  |  |  |  |
| 11  $(C_6H_5)_3P/$ | 1 | 1.65 | 44 | 14.5 | 100.0 | 23.0 | 200 | 147 |
| $(C_6H_5)_2P(CH_2)_2P(O)(C_6H_5)_2$: | 4 | 1.16 (0.93)[a] |  | 17.0 | 99.0 | 29.0 | 200 | 147 |
| (14:1 mole ratio) |  |  |  |  |  |  |  |  |
| 12  $(C_6H_5)_3P/$ | 1 | 1.24 | 30 | 11.5 | 100.5 | 24.0 | 200 | 147 |
| $(C_6H_5)_2P(CH_2)_2P(O)(C_6H_5)_2$: | 4 | 1.10 (0.87)[a] |  | 18.5 | 101.5 | 26.4 | 200 | 147 |
| (9:1 mole ratio) |  |  |  |  |  |  |  |  |
| 13  $(C_6H_5)_3P/$ | 1 | 1.05 | 11.4 | 9.5 | 100.0 | 35.5 | 200 | 120 |
| $(C_6H_5)_2P(CH_2)_2P(O)(C_6H_5)_2$: | 4 | 1.12 (0.93)[a] |  | 9.5 | 96.0 | 39.4 | 200 | 120 |
| (2:1 mole ratio) |  |  |  |  |  |  |  |  |

[a] The numbers in parenthesis correspond to the corrected reaction rate as explained above.
[b] The % catalyst activity decline is a measure of the decline in catalyst activity from Day 1 through Day 4 at 130° C. as computed by the formula $$\left(100 - \frac{\text{Corrected Reaction Rate for Day 4}}{\text{Observed Reaction Rate for Day 1}} \times 100\right)$$

The above data demonstrate that by employing mixtures of bis-phosphine monooxides and triarylphosphines (Examples 2, 4 and 6) significant thermal catalyst stability improvement is achieved relative to employing a triarylphosphine (Examples 1, 3 and 5). This thermal catalyst stability improvement is achieved with minimum loss of hydroformylation catalyst reactivity. Examples 9–13 show that by using mixtures of triphenylphosphine and bis-diphenylphosphino ethane monooxide ligands at different ratios result in varying degrees of catalyst reactivity and stability.

Surprisingly the observed effect obtained with the mixed phosphorus ligands is not due to the mere addition of the individual effects of the two ligands, but rather to an unforeseen cooperative effect as seen by the fact that both the bis-phosphine monooxide ligand by itself (Example 9) used at the equal phosphine/rhodium mole ratios employed in Example 13, and the triphenylphosphine ligand by itself (Example 1) at even higher phosphine/rhodium mole ratios than that employed in Example 13 show inferior thermal stability.

EXAMPLES 14 TO 18

A series of continuous propylene hydroformylation reactions were conducted in a similar manner as described in Examples 1 to 13 except that the following conditions were employed.

In each experiment about 20 ml. of a freshly prepared rhodium catalytic precursor solution was charged to the reactor with a syringe after purging the system with nitrogen. Each precursor solution contained about 200–300 ppm rhodium calculated as free metal introduced as rhodium dicarbonyl acetylacetonate, a phosphorus ligand or mixture of phosphorus ligands and Texanol ® as the solvent. The mole ratio of total free phosphorus ligand per mole of rhodium present in each precursor solution (P/Rh) and the mole ratio of each phosphorus ligand to each other in a given phosphorus mixture as shown in TABLE II below.

After closing the reactor, the system was again purged with nitrogen and the oil bath was heated to furnish the desired hydroformylation reaction temperature. The hydroformylation reaction in each experiment was conducted at a total gas pressure of about 165 psig, the target partial pressures of hydrogen, carbon monoxide and propylene being about 80 psia; 10 psia, and 30 psia, respectively, the remainder being nitrogen. The flows of the feed gases (carbon monoxide, hydrogen and propylene) were controlled individually with mass flow meters and the feed gases dispersed into the precursor solution via fritted glass spargers. The unreacted portion of the feed gases stripped out the product aldehydes. Each experiment was conducted at about 105° C. for two days and then the temperature raised to about 130° C. and the hydroformylation continued for 12 more days. During days 9 to 13 the carbon monoxide partial pressure was increased stepwise from about 10 to 25 psia and returned to about 10 psia for day 14. The product aldehydes for each experiment were analyzed over the sixth day of continuous operation at 130° C. and over the twelfth day of continuous operation at 130° C. and the average reaction rates for each experiment in terms of gram moles per liter per hour of total product aldehydes for the sixth and twelfth days of continuous operation at 130° C. and at the average measured partial pressures of hydrogen, carbon monoxide and propylene for said days are given in TABLE II below.

The corrected reaction rates given in parenthesis a in TABLE II below were computed using the formula Observed Reaction Rate for Day 12 at 130° C. $\times \frac{A}{B}$ wherein A equals the value of the given observed reaction rate for day 12 at 130° C. of the experiment divided by the predicted reaction rate for day 12 at 130° C. of continuous propylene hydroformylation at the same partial pressures and reaction conditions given for the observed reaction rate for day 12 at 130° C. of the experiment, using a mathematical rate model developed for a standard rhodium-triphenylphosphine complex catalyst; and B equals the value of the given observed reaction rate for day 6 at 130° C. of the experiment divided by the predicted reaction rate for day 6 at 130° C. of continuous propylene hydroformylation at the same partial pressures and reaction conditions given for the observed reaction rate for day 6 at 130° C. of the experiment, using a mathematical rate model developed for a standard rhodium-triphenylphosphine complex catalyst.

EXAMPLE 19

Propylene was continuously hydroformylated in a one gallon stainless steel autoclave employing a rhodium catalytic precursor solution containing about 300 ppm rhodium introduced as rhodium dicarbonyl acetylacetonate, about 19.2 weight percent triphenylphosphine, about 2.8 weight percent bis-diphenylphosphino ethane monooxide, and butyraldehyde as the solvent. The mole ratio of total phosphorus ligand per mole of rhodium in said precursor solution was about 300:1, while the mole ratio of triphenylphosphine to bis-diphenylphosphinoethane monooxide was about 10:1. A total gas pressure of about 194 psig and a $CO/H_2$/propylene pressure of about 10 psia carbon monoxide, about 90 psia hydrogen and 50–55 psia propylene was employed, the remainder being nitrogen and propane byproduct. The continuous hydroformylation process was carried out over about eleven days at about 130° C. Gaseous aldehyde products were stripped from the reactor and condensed, the recovered unreacted feed gases being recycled to the reactor via a gas compressor. The product aldehydes were collected, weighed and analyzed and the results are given in Table III below.

TABLE III

| Reaction Time (Hours) | Temp. °C. | Total Aldehyde Reaction Rate Gram Moles/ Liter Hour | [a]N/I Butyraldehyde Ratio | Propylene Partial Pressure (psia) |
|---|---|---|---|---|
| 26 | 130 | 3.79 | 12.2 | 50.4 |
| 45.5 | 130 | 3.95 | 12.0 | 53.6 |
| 69.5 | 130 | 4.35 | 11.1 | 50.2 |

TABLE II

| Example/Ligand | Day 130° C. | Aldehyde Product Reaction Rate gmoles/L hr | [b]% Activity Decline | $P_{CO}$ (psia) | $P_{H2}$ (psia) | $P_{C3H6}$ (psia) | [Rh] ppm | P/Rh Mole Ratio |
|---|---|---|---|---|---|---|---|---|
| 14 $(C_6H_5)_3P$ | 6 | 1.12 | 32 | 10.5 | 87.0 | 30.5 | 200 | 300 |
|  | 12 | 1.00 (.76)[a] |  | 9.5 | 102.0 | 32.0 | 200 | 300 |
| 15 $(CH_3—C_6H_4)_3P$ | 6 | 1.50 | 17 | 11.5 | 82.0 | 31.0 | 200 | 300 |
|  | 12 | 1.34 (1.24)[a] |  | 10.5 | 101.0 | 32.0 | 200 | 300 |
| 16 $(CH_3O—C_6H_4)_3P$ | 6 | 1.33 | 14 | 10.0 | 85.5 | 32.0 | 300 | 200 |
|  | 12 | 1.19 (1.14)[a] |  | 9.5 | 101.5 | 32.0 | 300 | 200 |
| 17 $(C_6H_5)_3P/$ | 6 | 1.28 | 28 | 10.5 | 84.0 | 41.0 | 300 | 230 |
| $(C_6H_{11})(C_6H_5)_2P$ (4:1 mole ratio) | 12 | 1.15 (.98)[a] |  | 10.5 | 102.0 | 44.0 | 300 | 230 |
| 18 $(C_6H_5)_3P/$ | 6 | 1.38 | 10.5 | 11.5 | 80.0 | 36.5 | 300 | 300 |
| $(C_6H_5)_2P(CH_2)_2P(O)(C_6H_5)_2$ (14:1 mole ratio) | 12 | 1.37 (1.23)[a] |  | 10.0 | 100.5 | 38.5 | 300 | 300 |

[a]The numbers in parenthesis correspond to the corrected reaction rate as explained above.
[b]The % catalyst activity decline is a measure of the decline in catalyst activity from Day 6 through Day 12 at 130° C. as computed by the formula $$\left( 100 - \frac{\text{Corrected Reaction Rate for Day 12 at 130° C.}}{\text{Observed Reaction Rate for Day 6 at 130 C.}} \times 100 \right)$$

The data in Table II above demonstrates that the rhodium complex catalyst of Example 18 using mixed triphenylphosphine-bis-diphenylphosphinoethane monooxide maintained its catalyst activity and stability much better over a wider range of carbon monoxide partial pressure than that of Examples 14, 15, and 16 which employed only a single triarylphosphine ligand as well as that of Example 17 which employed a mixture of triphenylphosphine and cyclohexyldiphenylphosphine.

| 93.5 | 130 | 4.33 | 11.2 | 50.9 |
| 165.5 | 130 | 3.91 | 11.4 | 53.2 |
| 189.0 | 130 | 3.74 | 11.7 | 54.0 |
| 213.5 | 130 | 3.75 | 12.1 | 54.7 |
| 239.0 | 130 | 3.53 | 11.9 | 55.0 |
| 262.5 | 130 | 3.49 | 12.2 | 54.6 |

[a]Number of moles of normal butyraldehyde per mole of branched butyraldehyde product.

The above data demonstrates the excellent catalyst stability and high aldehyde productivity obtained over about eleven days of continuous hydroformylation using a mixture of triphenylphosphine and bis-diphenylphosphinoethane monooxide ligand.

Various modifications and variations of this invention will be obvious to a worker skilled in the art and it is to be understood that such modifications and variations are to be included within the purview of this application and the spirit and scope of the appended claims.

What is claimed is:

1. A rhodium complex hydroformylation catalytic precursor composition consisting essentially of a solubilized rhodium carbonyl phosphorus acetylacetonate complex, and organic solvent, free triarylphosphine ligand and free organic tertiary bisphosphine monooxide ligand having the general formula

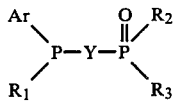

wherein Ar represents an identical or different substituted or unsubstituted aryl radical, and $R_1$, $R_2$ and $R_3$ group represents an identical or different substituted or unsubstituted monovalent hydrocarbon radical and Y represents a divalent bridging group; and wherein the mole ratio of free triarylphosphine ligand to free bisphosphine monooxide ligand present in said composition ranges from about 2:1 to about 30 to 1.

2. A composition as defined in claim 1, wherein the triarylphosphine ligand is triphenylphosphine and wherein in the bisphosphine monooxide formula, Ar represents an identical or different substituted or unsubstituted aryl radical containing from 6 to 12 carbon atoms; each $R_1$, $R_2$ and $R_3$ group represents an identical or different substituted or unsubstituted monovalent hydrocarbon radical containing from 1 to 30 carbon atoms and selected from the group consisting of alkyl, aryl, alkaryl, aralkyl and alicyclic radicals, and wherein Y represents a divalent bridging group containing from 1 to 30 carbon atoms selected from the group consisting of hydrocarbon radicals, oxygen containing hydrocarbon radials, sulfur containing hydrocarbon radicals and nitrogen containing hydrocarbon radicals.

3. A composition as defined in claim 2, which contains from about 50 to about 400 ppm rhodium calculated as free metal having been introduced as rhodium dicarbonyl acetylacetonate, a mole ratio of free triphenylphosphine to free bisphosphine monooxide ligand ranging from about 5:1 to about 15:1, and wherein the amount of solvent present ranges from about 5 percent by weight to about 95 percent by weight based on the total weight of said precursor composition.

4. A composition as defined in claim 3, wherein $R_1$, $R_2$ and $R_3$ represent a substituted or unsubstituted monovalent hydrocarbon radical selected from the group consisting of alkyl radicals having from 1 to 12 carbon atoms and aryl radicals having from 6 to 12 carbon atoms, and wherein Y contains from 1 to 12 carbon atoms.

5. A composition as defined in claim 4, wherein Ar is an unsubstituted aryl radical; $R_1$, $R_2$ and $R_3$ represent unsubstituted alkyl or aryl radicals, and Y is a divalent hydrocarbon radical.

6. A composition as defined in claim 5 wherein said organic tertiary bisphosphine monooxide ligand is a ligand having the formula

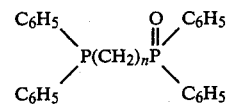

wherein n is an integer of 2 to 8.

7. A composition as defined in claim 6, wherein n is 2.

* * * * *